(12) United States Patent  
Chalmers et al.

(10) Patent No.: US 8,440,800 B2  
(45) Date of Patent: May 14, 2013

(54) COMPOSITIONS FOR REDUCING CELL ADHESION TO BUBBLES

(75) Inventors: Jeffrey J. Chalmers, Columbus, OH (US); James F. Rathman, Columbus, OH (US); Weiwei Hu, San Diego, CA (US)

(73) Assignee: The Ohio State University Research Foundation, Columbus, OH (US)

( * ) Notice: Subject to any disclaimer, the term of this patent is extended or adjusted under 35 U.S.C. 154(b) by 585 days.

(21) Appl. No.: 12/438,681

(22) PCT Filed: Aug. 27, 2007

(86) PCT No.: PCT/US2007/018827  
§ 371 (c)(1),  
(2), (4) Date: Jun. 18, 2010

(87) PCT Pub. No.: WO2008/027337  
PCT Pub. Date: Mar. 6, 2008

(65) Prior Publication Data  
US 2010/0261272 A1    Oct. 14, 2010

Related U.S. Application Data

(60) Provisional application No. 60/840,552, filed on Aug. 28, 2006.

(51) Int. Cl.  
*C07H 15/00* (2006.01)  
*C07H 15/04* (2006.01)  
*C07H 15/18* (2006.01)

(52) U.S. Cl.  
USPC .......................................................... 536/4.1

(58) Field of Classification Search .................. None  
See application file for complete search history.

(56) References Cited

U.S. PATENT DOCUMENTS 5,384,128 A    1/1995  Meezan et al.  
2008/0207532 A1*  8/2008  Huang et al. .................. 514/25

OTHER PUBLICATIONS

Merriam-Webster's Collegiate Dictionary, published 1999 by Merriam-Webster, Incorporated, p. 924.*  
Koeltzow et al. Preparation and Properties of Pure Alkyl Glucosides, Maltosides and Maltotriosides, JAOCS, vol. 61, No. 10, p. 1651 (Oct. 1984).  
PCT International Search Report and the Written Opinion of the International Searching Authority, Date of mailing: Aug. 7, 2008, International Application No. PCT/US07/18827, International Filing Date: Aug. 27, 2007.  
PCT International Preliminary Report on Patentability (Chapter I of the Patent Cooperation Treaty), Date of mailing: Mar. 12, 2009, International Application No. PCT/US07/018827, International Filing Date: Aug. 27, 2007.  
Chisti, Animal-Cell Damage in Sparged Bioreactors, TIBTECH Oct. 2000, vol. 18, pp. 420-432.  
Koeltzow et al., Preparation and Properties of Pure Alkyl Glucosides, Maltosides and Maltotriosides, JAOCS, vol. 61, No. 10 (Oct. 1984) pp. 1651-1655.  
Michaels et al., Analysis of Cell-to-Bubble Attachment in Sparged Bioreactors in the Presence of Cell-Protecting Additives, Biotechnology and Bioengineering, vol. 47, pp. 407-419 (1995) John Wiley & Sons, Inc.  
Rojas et al., Viscoelastic Properties of Isomeric Alkylglucoside Surfactants Studied by Surface Light Scattering, J. Phys. Chem. B 2005, 109, 22440-22448.  
Soderlind et al., Haemolytic activity of maltopyranoside surfactants, European Journal of Pharmaceutics and Biopharmaceutics 62 (2006) 254-259.  
Wu, Mechanisms of animal cell damage associated with gas bubbles and cell protection by medium additives, Journal of Biotechnology 43 (1995) 81-94.  
European Search Report, Application No./ Patent No. 07837381.8-2403 / 2057265 PCT/US2007018827, Date Feb. 12, 2009.

* cited by examiner

*Primary Examiner* — Eric S Olson  
(74) *Attorney, Agent, or Firm* — MacMillan, Sobanski & Todd, LLC

(57) ABSTRACT

Compositions and methods for reducing gas-cell surface interface damage include a protective composition having at least sugar moiety where the sugar moiety provides a hydrophilic component to the protective composition.

18 Claims, 6 Drawing Sheets

COMPOSITIONS FOR REDUCING CELL ADHESION TO BUBBLES

CROSS-REFERENCE TO RELATED APPLICATIONS

This application claims the benefit of the PCT/US07/018,828 filed Aug. 27, 2007, which claims priority to the U.S. Provisional Application No. 60/840,552 filed Aug. 28, 2006, the disclosure of which is incorporated herein by reference.

GOVERNMENT SUPPORT

This invention was supported, in whole or in part, by grants from NIH-NCI Grant/Contract Number RO1 CA62349, NIH-NIAID Grant/Contract Number 1 R01 AI056318-01, and NCI Grant/Contract Number 1 R01 CA97392-01A 1. The Government has certain rights in this invention.

BACKGROUND OF THE INVENTION

Mammalian cell culture has emerged to become an indispensable technology for the production of a number of the desirable end products. Non-limiting examples of such desirable end products include human therapeutic biologicals and/or biomass materials, which are made in large-scale animal cell cultures grown in bioreactors. In some cases, the demand for these biologicals and/or biomass materials is on the order of tens to hundreds of kilograms per year, making mammalian cell culture on the scale of 10,000 liters, or higher, routine.

The bioreactors are designed especially for mammalian cell culture and for their ability to support cell growth and end product production under batch culture conditions. The industry has experienced challenges, however, in achieving maximum viable cell densities and desired end-product production. Differences in vessel and agitator geometry and aeration modes of operation have not completely solved this problem.

It is believed that one cause of such limitations in the scaled-up processes is due, at least in part, to the loss of cells due to lethal, mechanical damage in the growth vessels. This lethal damage is generally believed to be the result of hydrodynamic and interfacial forces acting on the cells and these stresses influence both the viability and specific production rate of the cells and thus the overall productivity of the reactors.

In certain conditions, this cell death is caused by the attachment of cells to gas-liquid interfaces at the top surfaces of the vessels where the aqueous media, gas bubbles (typically introduced in the bottom of the vessel and subsequently rise to the top), and air and/or gas above the aqueous media come into contact. Hydrodynamic and interfacially driven forces are very high at these interfaces, especially when a bubble ruptures, but is also high in the foam layer where bubbles drain and coalesce.

It has been experimentally reported that under certain conditions, the presence of cells attached to bubbles is a major cause of cell death in sparged cell cultures. The cells that die, for example, during the bubble burst can come from three sources: cells suspended near the bubble; cells trapped in the bubble lamella; and cells that attached to the rising bubble. This cell attachment can depend on cell radius, bubble radius, and cell-bubble attachment time.

In addition, there are concerns with respect to potential cell damage as a result of gas sparging and foam formation that can occur in large scale-up productions. This is especially true as cell concentrations during such scale-ups can increase to 10 million cells per milliliter and higher in fed-batch and perfusion cultures.

Another concern is the interactions among cells, bubbles that form and disperse within the cell cultures. This becomes of increasing importance, as there is a greater demand for the safe, effective and efficient design and operation of large-scale production of biologicals and/or biomass materials from cell cultures. Another concern is how to develop protective additives that can be useful over a wide range of additive conditions and cell concentrations.

Many researchers have observed sparging-related cell damage. These reports all underscore the concept that cell-bubble interactions play a much more important role in physical cell damage than pure agitation.

In particular, the high demand for some of these end products, such as antibodies, has inevitably lead to the requirement of more efficient manufacture processes, particularly high productivity and high cell density. However, mammalian cells are sensitive to the surrounding environment, including the concentration of ammonia, lactate, dissolved carbon dioxide osmolality, and pH. Nevertheless, through careful and systematic development, industrial fed-batch or perfusion cell culture processes have been able to increase product titers, from typically around 50 mg/L to over 5 g/L over a two decade period.

Along with a better understanding of cell metabolism from a biological perspective, significant efforts have been made to explore physical challenges in mammalian cell culture, including mixing, mass transfer, and cellular sensitivity to hydrodynamic forces. While a number of systems have been proposed for large scale culture, the stirred tank bioreactor with gas sparging is the commercial system of choice. Such a system, while simpler to implement and operate than other more complex systems, creates gas-liquid-solid (cell) multiphase environments within the vessel.

The presence of surface-active compounds, including surfactants and proteins, makes these interfaces highly complex; however, these interfaces are fundamental to the gas-liquid mass transfer ($O_2$ supplement and $CO_2$ removal). Unfortunately, these gas-liquid-cell interfaces (cell-gas adhesion, foam formation, cells trapping with in the foam, and protein/lipid adhesion to gas-liquid-solid interfaces) also occur when sparging is used. Unfortunately, the current understanding of interfacial phenomena in cell culture processes is predominately based on empirical studies. In particular, a number of additives have been examined for their protective effect on bubble-associated cell damage. These additives include, for example, fetal bovine serum (Kunas and Papoutasakis, 1989); the Pluronic® series of surfactants (Murhammer and Goochee, 1990); methyl cellulose (Goldblum et al., 1990), Dextran (van der Pol et al., 1995), polyethylene glycol (Michaels and Papoutsakis, 1991) and polyvinyl alcohol (Michaels et al., 1992). Among them, the Pluronic F-68® (PF-68®) surfactant, first advocated in the 1960's, is still the most commonly used additive (Swim and Parker, 1960; Runyan and Geyer, 1963; Kilburn and Webb, 1968). There is no doubt that the PF-68® surfactant contributes significantly (potentially vital) to the success of industrial mammalian cell culture in bioreactors.

The PF-68™ material is a nonionic surfactant with triblock structure consisting of hydrophobic polypropylene oxide) center and two hydrophilic poly(ethylene oxide) tails, and which does not have a distinct critical micelle concentration (CMC). It has an average molecular weight of 8400. Even though a number of protective mechanisms of the Pluronic PF-68® surfactant have been proposed (Chisti, 2000; Wu, 1995), the ability of the PF-68® material to inhibit cell-bubble attachment is considered the primary mechanism. Chattopadhyay et al. (1995b), suggested that this inhibition of cell-interface adhesion is the result of the PF-68® material significantly decreasing the surface tension of the gas-liquid interface such that adhesion to the gas-liquid interface is thermodynamically unfavorable. The interaction and structure of block, non-ionic copolymers (such as PF-68®) with air-water interfaces is a subset of a significant area of research in the general areas of surfactants and air/water interface interactions.

With respect to cells, Ma et al. (2004) recently quantitatively studied the interactions among cells, bubbles, and PF-68® over a broad range of PF-68® and PER.C6® cell concentrations. The cell concentration in the foam liquid decreased dramatically with the increase of PF-68™ concentration; however, as the cell concentration increased (on the order of $10^7$ cells/ml, or higher) even at high PF-68 concentration of greater than 1 g/L, over 1000 PER.C6® per bubble became trapped in the foam layer.

As the final cell concentration of commercial mammalian cell culture systems continue to increase, it is apparent that the effectiveness of the PF-68® surfactant will diminish. While it can be argued that one can tolerate some loss of productivity of a relatively small number of cells in the foam, even the lysis of this small number, with the subsequent release of the intracellular components into the media is an unwelcomed occurrence. In addition, it is highly desirable to have other, effective, alternatives to the PF-68® surfactant.

In addition to their intended function at gas-liquid interfaces, surfactant additives can have a significant effect on the cell membrane. The mammalian cell membrane is a presumably thermodynamically-controlled and self-assembled bilayer consisting of phospholipids, triglycerides, cholesterol, and trans-membrane proteins. The membrane structure is dynamic with the lateral diffusion and flip-flop of lipid components occurring. It is generally believed that specific surfactants can efficiently compete with the interactions between membrane lipids and proteins, ranging from incorporation and/or partitioning of the surfactant into the cell membrane, to the outright dissolving of the membrane structure (Neimert-Andersson et al. 2006).

Therefore, one of the most important criteria with respect to a material that will prevent negative cell gas adhesion is that such material should not be harmful to mammalian cells. At least two mechanisms have been proposed to explain the most harmful of surfactant interactions beyond direct plasma membrane solubilization: flip-flop and micellar attack (Maire et al., 2000). In the former, non-micellar surfactants penetrate the membrane and cause damage by disrupting the cell membrane structure, including flipping lipids inside out. In the latter, membrane compounds are transferred directly from the outer side of membrane bilayer into surfactant micelles. In spite of the importance of surfactants to protect, and alternatively, solubilize mammalian cells, the selection of surfactants, both with respect to type and concentration selection and optimization is still a semi-empirical process.

In yet another area or research, despite a fundamental understanding of the interactions of surfactants with cells, and specific molecules of interest (i.e., hydrophobic nutrients and drugs), significant interest exists in the drug delivery research community to further develop surfactants that solubilize drugs with low water solubility, yet do not cause any cellular damage. Historically, polyoxyethylene-based surfactants have been one type of surfactant used for this purpose; however, there are number of disadvantages. Consequently, a number of studies exist investigating, and suggesting, other surfactants for drug delivery. Thus, while there is a different purpose than the prevention of cell adhesion to gas medium interfaces, many of the attributes required for an optimum drug delivery surfactant are similar to prevention of cell adhesion surfactant.

The discussion of various publications cited herein and other prior knowledge does not constitute an admission that such material was published, known, or part of the common general knowledge.

SUMMARY OF THE INVENTION

In one aspect, there is provided herein one or more compositions for reducing gas-cell surface interface damage in a cell culture. Also, the protective composition substantially prevents adherence of gas bubbles to the cell and/or the cells to gas-liquid interfaces.

The protective compositions have at least one sugar moiety that provides a hydrophilic component to the protective composition.

In certain embodiments, the protective compositions comprise one or more low molecular weight, closed ring sugars. In certain non-limiting examples include one or more of octyl-maltopyranoside (OM), nonyl-maltopyranoside (NM), decyl-maltopyranoside (DM), and cyclohexyl-butyl-maltopyranoside (Cymal-4® or CM4).

In another aspect, there is provided herein a method for protecting cells from gas-bubble associated damage or from medium-air interface damage. In particular, the method includes culturing cells in the presence of an effective amount of one or more protective compositions as described herein.

The above summary of the present invention is not intended to describe each disclosed embodiment or every implementation of the present invention.

The description that follows more particularly exemplifies illustrative embodiments. In several places throughout the application, guidance is provided through lists of examples, which examples can be used in various combinations. In each instance, the recited list serves only as a representative group and should not be interpreted as an exclusive list. Furthermore, various embodiments are described in which the various elements of each embodiment could be used in other embodiments, even though not specifically described.

As such, various objects and advantages of this invention will become apparent to those skilled in the art from the following detailed description of the preferred embodiment, when read in light of the accompanying drawings.

BRIEF DESCRIPTION OF THE DRAWINGS

FIGS. 1a-1f shows the chemical structures of examples of the different groups of molecules tested:

FIGS. 1a and 1b present structures of various comparative materials, i.e., glucopyranosides: FIG. 1a shows n-octyl-β-glycopyranoside (OG), and FIG. 1b shows n-decyl-β-glycopyranoside (DG);

FIGS. 1d, 1e, 1f and 1g present structures of various protective compositions, i.e., maltopyranosides: FIG. 1d shows n-octyl-β-maltopyranoside (OM), FIG. 1e shows n-decyl-β-maltopyranoside (DM), FIG. 1f shows n-nonyl-β-maltopyranoside (NM), and FIG. 1g shows 4-cyclohexyl-1-butyl-β-maltopyranoside (CM4).

DETAILED DESCRIPTION OF THE PREFERRED EMBODIMENT(S)

Reference will now be made in detail to various exemplary embodiments of the invention. These exemplary embodiments are provided to better explain certain details that may apply to some aspects of the invention, but are not to be considered as limiting the scope of the invention to any particular configuration of composition components or method steps.

In a first aspect, the invention provides a composition for reducing the adhesion of cells to bubbles, or gas-liquid interfaces in general. The composition generally has hydrophilic sugar moiety, has a low molecular weight and is non-ionic. It has been surprisingly found that the use of several low molecular weight compounds provides a composition that can be used for greatly reducing adhesion of cells in scaled-up production of biologicals without significant degradation of the cell culture. It has also been surprisingly found that the composition is suitable as a component of culture media for the continued growth of such cell cultures on a commercial scale.

In another aspect, there is provided herein a method that is superior to the current and, at times, inefficient methods of bioreactor operation. The method described herein applies an advanced process control methodology to the cell culture process variables. The present method controls the cell culture process variables that influence and control cellular growth dynamics during bioprocessing and cell culturing.

The cells that can be protected with the composition described herein can be any prokaryotic or eukaryotic cell. The cell can be any cell of interest, including, but not limited to, mammalian cells, avian cells, amphibian cells, reptile cells, insect cells, and plant cells. For example, the cell can be a human cell, a monkey cell, a rat cell, a mouse cell, a dog cell, a cat cell, a pig cell, a horse cell, a hamster cell, a rabbit cell, a frog cell, or an insect cell.

By the term "at least one cell", it is meant not only a single cell, but a single cell type. Thus, two or more cells can mean not only two or more cells of the same cell type, but one or more cell of two different cell types.

Unless otherwise specifically noted, it is not relevant whether a population of a single cell type is present or a population of two or more cell types is present. Regardless, the methods described herein (including those discussed below) will provide the stated effects. Furthermore, the term "at least one cell" and "a cell" are, unless otherwise noted, used interchangeably herein to define a single cell, a collection of a single type of cell, or a collection of multiple types of cells, at least one cell of each type being present.

Thus, in one broad aspect, there is provided herein a protective composition for reducing gas-cell surface interface damage. The protective composition substantially prevents adherence of gas bubbles to the cell and/or the cells to gas-liquid interfaces. The protective composition has at least sugar moiety therein that provides a hydrophilic component to the protective composition.

In certain embodiments, the sugar moiety has at least two, or in other embodiments, three closed rings. Also, in certain embodiments, the sugar moiety includes at least one oxygen on a backbone. The oxygen is bonded to at least one saturated or unsaturated carbon chain to which hydrocarbon ring is also bonded.

In certain other embodiments, the sugar moiety includes at least one oxygen on a backbone thereof. The sugar moiety includes at least one oxygen on a backbone thereof, and the oxygen is bonded to at least one saturated or unsaturated carbon chain.

In a particular embodiment, the sugar moiety comprises a maltopyranoside or a maltoside. In one non-limiting example, the sugar moiety comprises an alkyl-β-D-maltoside, as shown in FIG. 1c which shows an alkyl-β-D-maltoside, where n can range from 1-15; and in certain embodiments from 6 to 10. The alkyl moiety in the alkyl-β-D-maltoside can be a saturated or unsaturated, substituted or unsubstituted, straight, branched or ring hydrocarbon.

Also, the protective composition can be present in an amount effective to reduce gas-cell interface damage; in certain non-limiting examples, the amount can range from about 0.1 g/L to about 4.0 g/L.

In particular embodiments, the protective composition can comprises at least one of: n-Octyl-β-D-maltopyranoside (OM), n-Nonyl-β-D-maltopyranoside (NM), n-Decyl-β-D-maltopyranoside (DM), and cyclohexyl-butyl-maltopyranoside (CM-4). In certain embodiments, the protective composition can comprise one or more of: about 3.5 g/L or less octyl maltopyranoside; about 1.0 g/L or less nonyl maltopyranoside; about 0.28 g/L or less decyl maltopyranoside; and about 1.5 g/L or less cyclohexyl-butyl-maltopyranoside (CM-4).

In another broad aspect, there is provided herein a method for protecting cells from gas-bubble associated damage which comprises culturing cells in the presence of an effective amount of one or more protective compositions of any of the preceding claims.

There is also provided herein a method of modifying a cellular surface so as to confer resistance to adherence of cells to gas bubbles in a medium containing one or more cells. Such method can comprise adding to the medium an effective amount of at least one protective composition under conditions in which the protective composition substantially prevents adherence of gas bubbles to the cell.

In another broad aspect, there is provided herein a method for recovering one or more desired products from host cells comprising: i) providing a source of cells having or producing at least one desired product; ii) providing a protective composition as described herein; and iii) contacting at least a some of the cells with the protective composition in an amount effective to reduce adhesion of one or more gas bubbles to the cells. The cells can be prokaryotic or eukaryotic cells; non-limiting examples include bacterial, yeast, insect, animal, algae or plant cells.

In another aspect, there is provided herein kits. In general, the kits contain a composition of the invention. The kits can further comprise one or more substances, materials, reagents, etc. that can be used for the culturing of cells. In certain embodiments, some or all of the materials, reagents, etc. necessary to culture the cells are included in the kit.

For example, a kit may contain a container holding a buffer and at least one protective composition, and, in the same or a separate container, at least one reagent for culturing the cells. The kits can comprise the components in a single package or in more than one package within the same kit. Where more than one package is included within a kit, each package can independently contain a single component or multiple components, in any suitable combination.

The invention, in general, is suitable for use in both research and in scale-up processes. Thus, the compositions and methods have human health, nutra chemicals, food, agricultural and veterinary applications.

In a particular aspect, there are provided herein biological culture protective compositions that are comprised of one or more low molecular weight closed ring sugar-based compositions. The protective compositions are especially useful in reducing cell damage due to bubbles bursting in the culture media. The protective compositions also aid in the continued growth of the culture is scaled-up applications.

The protective compositions have several advantages over the standardly used material, Pluronic F-68®, which is a high molecular weight surfactant. In a particular aspect, the protective compositions, as described herein, have molecular weights that are generally substantially smaller than the desired end products that are to be harvested from the cell culture. Thus, the use of such protective compositions not only allows the cell culture to undergo increased cell growth, but also further reduces detrimental separation difficulties that could occur in the various downstream processes where the desired end product is harvested from the cell culture. The molecular weights of especially useful protective compositions, as described herein, are on the order of several hundred, as opposed to about 8,400 Mol. Wt. or more for Pluronic F-68® surfactant and 10,000 Mol. Wt. or greater for other surfactants.

EXAMPLES

The invention will be further explained by the following Examples, which are intended to be purely exemplary of the invention, and should not be considered as limiting the invention in any way.

It is to be noted at this point that each value stated in this disclosure is not, unless otherwise stated, meant to be precisely limited to that particular value. Rather, it is meant to indicate the stated value and any statistically insignificant values surrounding it. As a general rule, unless otherwise noted or evident from the context of the disclosure, each value includes an inherent range of 5% above and below the stated value. At times, this concept is captured by use of the term "about". However, the absence of the term "about" in reference to a number does not indicate that the value is meant to mean "precisely" or "exactly". Rather, it is only when the terms "precisely" or "exactly" (or another term clearly indicating precision) are used is one to understand that a value is so limited. In such cases, the stated value will be defined by the normal rules of rounding based on significant, digits recited. Thus, for example, recitation of the value "10" means any whole or fractional value between 9.5 and 10.5, whereas recitation of the value "exactly 100" means 99.5 to 100.4.

The term "bubble" as used herein refers to a volume of gas generally in the shape of a sphere within a fluid wherein the gas comprises vapors of the liquid component of the fluid, dissolved gas in the fluid or a combination thereof.

Materials and Methods

Cytotoxicity Study.

Chinese Hamster Ovary cells (CHO) cell line K1 (ATCC CCL-61) were used. The cells were initially cultured in Ham F-12 culture medium supplemented with 10% v/v fetal bovine serum (Sigma Aldrich Co., St. Louis, Mo.) in T-75 flasks. Then the cells were gradually adapted to chemically-defined medium (CD CHO-A, Invitrogen, Carlsbad, Calif.), which contain no PF-68. The cells were subcultured every 3-4 days and maintained at 37° C. incubator with 5% $CO_2$. All the cultures were anchorage-dependent.

Materials Tested.

A mass screening experiment was performed on the following surfactant comparative materials: SOS, SDeS, SDS, DDeAO, DDAO, DTAB, DDAO DTAB, CTAB, and PF-68® (purchased from Sigma Aldrich Company, St. Louis, Mo.).

Also tested were the protective compositions: OG, OM, OT, DG, DM, NM, and CYMAL®-4 (purchased from Anatace Inc. Maumee, Ohio). Table 1 herein presents the chemical name, abbreviated name, molecular weight, CMC concentration, the Alkyl chain length, and type of molecule. In Table 1, the surfactant comparative materials and the protective compositions are grouped by same type of head group and increasing alkyl chain length.

Figure 1A:
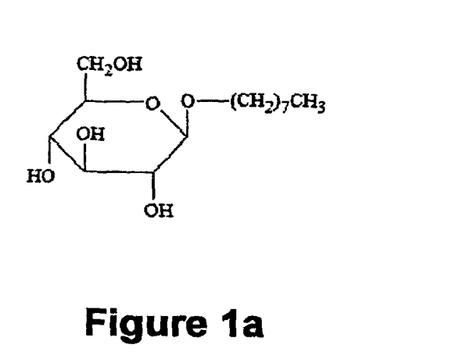
Figure 1B:
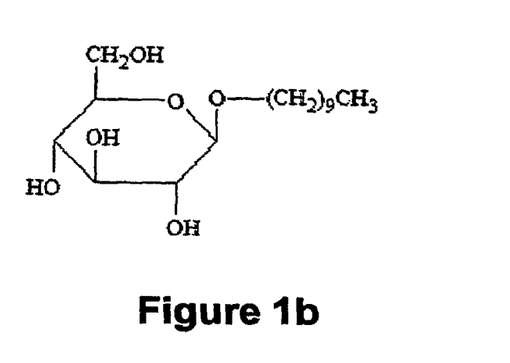
Figure 1C:
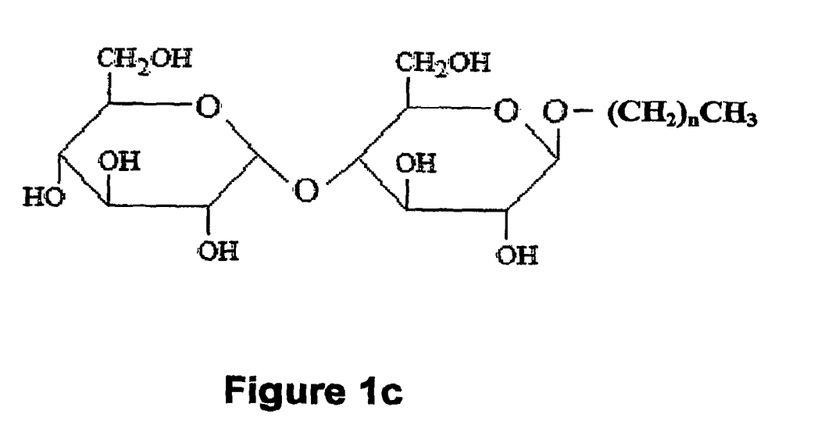
FIG. 1c shows an alkyl-β-D-maltoside, where n can range from 0-15.

FIGS. 1a and 1b present structures of various comparative materials, i.e., glucopyranosides: FIG. 1a) shows n-octyl-β-glycopyranoside (OG), and FIG. 1b) shows n-decyl-β-glycopyranoside (DG).

Figure 1D:
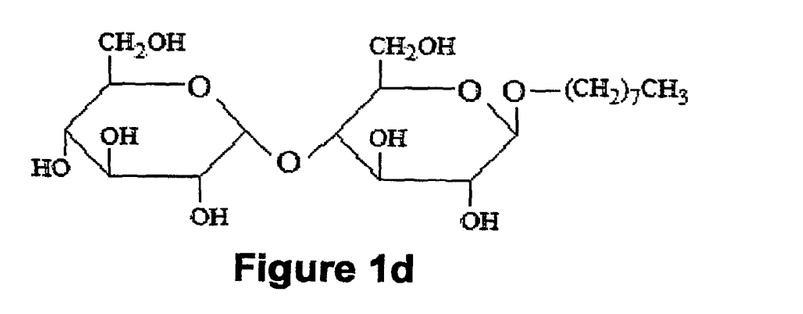
Figure 1E:
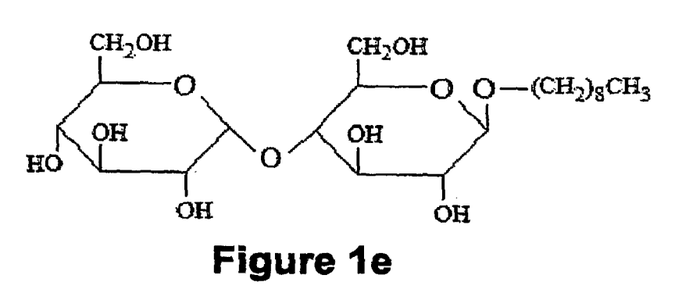
Figure 1F:
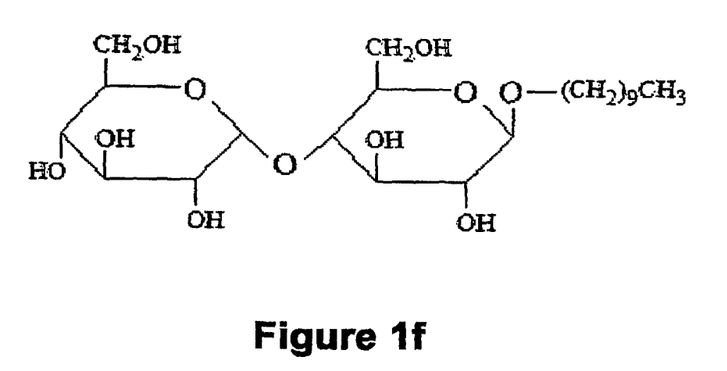
Figure 1G:
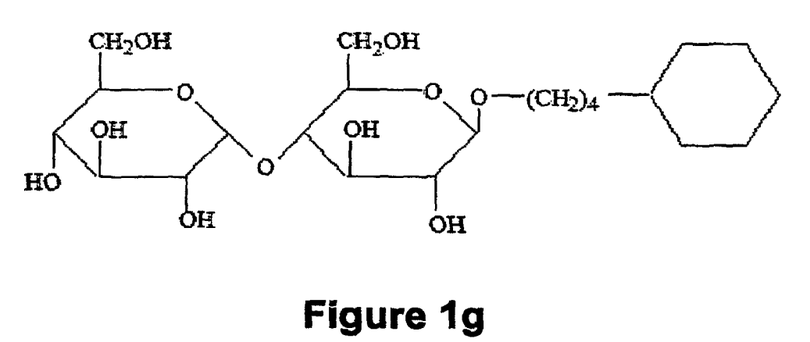

FIGS. 1d, 1e, 1f and 1g present structures of various protective compositions, i.e., maltopyranosides: FIG. 1d) shows n-octyl-β-maltopyranoside (OM), FIG. 1e) shows n-decyl-β-maltopyranoside (DM), FIG. 1f) shows n-nonyl-β-maltopyranoside (NM), and FIG. 1g) shows 4-cyclohexyl-1-butyl-β-maltoside (CM4).

One measure of the characterization of surfactants is the critical micelle concentration (CMC). Surfactants consist of a hydrophilic head and a hydrophobic tail. For example, when a surfactant is added to water, the surfactant initially enriched itself at the surface, i.e., the hydrophobic tail projects from the surface. Only when the surface has no more room for further surfactant molecules will the surfactant molecules start to form agglomerates inside the liquid. These agglomerates are known as micelles. The surfactant concentration at which micelle formation begins is known as the critical micelle formation (CMC). Micelles are spherical or ellipsoid structures on whose surface the hydrophilic heads of the surfactant molecules are gathered together whereas the hydrophobic tails project inwards.

A number of materials, at a number of concentrations were tested to determine the ability of the material to damage/inhibit cell growth.

Fluorescent Cytotoxicity Studies.

The materials were compared at the same concentration relative to the specific surfactants critical micelle concentration, CMC, i.e., 0.01 CMC or 0.1 CMC. In order to minimize the effect of potential adsorption during filter sterilization, the concentrated material solutions were applied, and then diluted to desired concentration at time of use. The surface tensions before and after filtration did not show significant difference (data not shown).

Black, clear-bottom 96-well plates (Fisher Scientific, Hampton, N.H.) were used in the screening experiments. In each well, 150 μl cell suspensions with a total cell number of approximately $10^4$ were inoculated along with the test materials and subsequently cultured in a 37° C. incubator with 5% $CO_2$. After 48 hours, the supernatant was carefully removed while the attached CHO cells remained at the bottom of the well. 100 μl of 4 μM calcein AM solution (Invitrogen, Carlsbad, Calif.), a fluorescence probe, was added to each well and incubated for one hour at 37° C. in order to quickly assess cell growth (Yang et al., 2002). Calcein AM is an esterase substrate which can be converted into a polar, fluorescent product by an intracellular enzyme. The fluorescence density was read by a Cytofluor 4000 (Applied Biosystems, Foster City, Calif.). Six replications were performed for each condition (type of material and concentration) and the positions on the 96 well plates were randomized. A reasonable linear relationship between cell number (less than $5 \times 10^5$ per well) and fluorescence density was confirmed before screening experiments; however, a control was created with each specific experiment.

Cytotoxicity Studies in T25 Flasks.

Various candidate materials from the 96 well plate assays were further investigated using T25 flasks. The concentration of the candidate materials were tested at discrete concentration, which depended on the specific material, but at the highest concentration exceeded 0.1 CMC. In all cases, tested, a concentration at which cell growth began to be inhibited was detected.

Additional protective compositions, Nonyl maltopyranoside (NM) and CYMAL®-4 (CM4), were purchased from Anatace Inc. (Maumee, Ohio). The inoculation was $3.0 \times 10^5$ cells/ml. After 48 hours, the cells were harvested by Accutase® (Innovative Cell Technologies Inc., San Diego, Calif.) and counted by a hemocytometer. Besides cell growth, the morphology of cells was also monitored by an inverted microscope (Nikon Ecllipse TE2000-U, Melville, N.Y.).

Surface Tension Measurements.

The CMC depends on temperature and solution components. Given the significant number of components in typical cell culture media, the CMC of the comparative materials and the protective compositions were determined at 37° C. and in CD CHO-A medium using a SensaDyne bubble tensiometer PC500L (Chem-Dyne Research Corporation, Mesa, Ariz.), which uses the maximum bubble pressure method. The time between initial bubble formation and attainment of maximum bubble pressure, "surface age", can be varied by changing the gas flow rate. When the static surface tensions were measured, the surface age were adjusted to approximate 1 s, which was enough for small molecule surfactants to migrate to the bubble surface and potentially reach equilibrium. When the dynamic surface tensions were measured, the surface age was varied in the range of about 0.1 to about 3.0 seconds.

Bubble-Cell Interactions.

An improved bubble collector device described by Ma et al. (2004) was used to quantitatively study cell entrapment in the foam. Specifically, this device can isolate bubble rupture events from foam formation vessel as well as maintain a plug-flow of bubbles from the foam layer into the bubble collection tube.

Consequently, the cell suspension/supernatant in the collection tube is only from the foam or bubble ruptures (i.e. bubbles do not rupture directly above the cell suspension). The cell concentration was determined using the lactate dehydrogenase (LDH) assay (CytoTox 96, Promega, Madison, Wis.). 9% (w/v) Triton X-100 solution was added to the cell suspension to be evaluated at a ratio of 1 to 10, and subsequently incubated at 37° C. for 45 minutes in order to lyse all the cells. A standard curve between LDH absorption and cell concentration by hemocytometer measurement was made for each set of experiments. The foam liquid volume was also measured by weighing the collect tube before and after experiments, assuming a liquid density of 1.0 g/ml.

For the bubble column studies, CHO K1 cells, grown in CD-CHO medium, were harvested during exponential phase of growth in spinner flasks. Multiple cycles of centrifugation and re-suspension in PBS were performed in order to remove PF-68 originally present in the medium. Finally, the cells were re-suspended in PBS solution with the desired surfactant concentration and loaded into the bubble collector.

The initial cell concentration was approximately $0.8 \times 10^6$ cells/ml with a high viability (>95%). A 1.0 ml foam layer was built up which then flowed out the exit tube and collected into the 15 ml centrifuge tubes. The gas flow rate was controlled at 2.5 ml/min by an automatic syringe pump (PHD 2000, Harvard Apparatus, Holliston, Mass.). No cell sedimentation was observed.

Two spargers, a 22 gauge needle and a sintered glass (ACE glass, Vineland, N.J.) provided bubbles which produced, as expected, two different bubble sizes. The bubbles sizes were determined using a SCIMAX CCD digital camera (MVIA, Monaca, Pa.) and an infinity lens (ISCO Precision Optics GMBH, Germany) in a glass square column. The cell enrichment factor can be defined as the ratio of total LDH concentration in the foam liquid to that in the bulk liquid after lysing all the cells.

Results

Effect of Surfactants on Cell Growth.

The initial, 96 well plate screening studies focused on the first 12 materials listed in Table 1 which contains a list of various properties of the comparative material and the protective compositions:

TABLE 1

| | Abbreviated Name | Mol. Wt. | CMC (mM) | Alkyl Chain Length | Type |
|---|---|---|---|---|---|
| Comparative Materials | | | | | |
| Sodium octyl sulfate | SOS | 232 | 85.6 | 8 | anionic |
| Sodium decyl sulfate | SDeS | 260 | 12.2 | 10 | anionic |
| Sodium dodecyl sulfate | SDS | 288 | 2.3 | 12 | anionic |
| N,N-Dimethyldecyl amine N-oxide | DDeAO | 201 | 6.4 | 10 | nonionic |
| N,N-Dimethyldodecyl amine N-oxide | DDAO | 229 | 2.0 | 12 | nonionic |
| Dodecyltrimethyl ammonium bromide | DTAB | 308 | 7.0 | 12 | cationic |
| Hexadecyltrimethyl ammonium bromide | CTAB | 364 | 1.3 | 16 | cationic |
| n-Octyl-β-D-thioglucopyranoside | OT | 308 | 11.0 | 8 | nonionic |
| n-Octyl-β-D-glucopyranoside | OG | 292 | 27.1 | 8 | nonionic |
| n-Decyl-β-D-glucopyranoside | DG | 320 | 2.3 | 10 | nonionic |
| Protective Compounds | | | | | |
| n-Octyl-β-D-maltopyranoside | OM | 455 | 24.5 | 8 | nonionic |
| n-Nonyl-β-D-maltopyranoside | NM | 468.5 | 6 | 9 | nonionic |

TABLE 1-continued

| | Abbreviated Name | Mol. Wt. | CMC (mM) | Alkyl Chain Length | Type |
|---|---|---|---|---|---|
| n-Decyl-β-D-maltopyranoside | DM | 483 | 1.8 | 10 | nonionic |
| 4-Cyclohexyl-1-butyl-β-D-maltoside | CYMAL-4 ® | 480.5 | 7.6 | 4 | nonionic |

Figure 2:
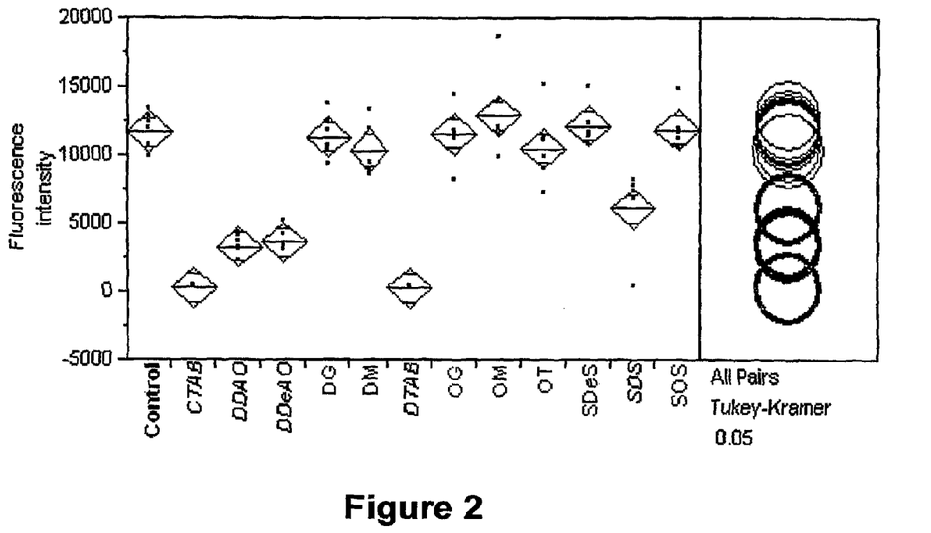
FIG. 2 is a graph showing the potential of various compositions to damage/inhibit cell growth as measured by specific viability dyes and fluorescence intensity measurements. In the comparison of cytotoxicity at 0.01 CMC, red color represents the conditions with no significant difference with respect to the control.
Figure 3:
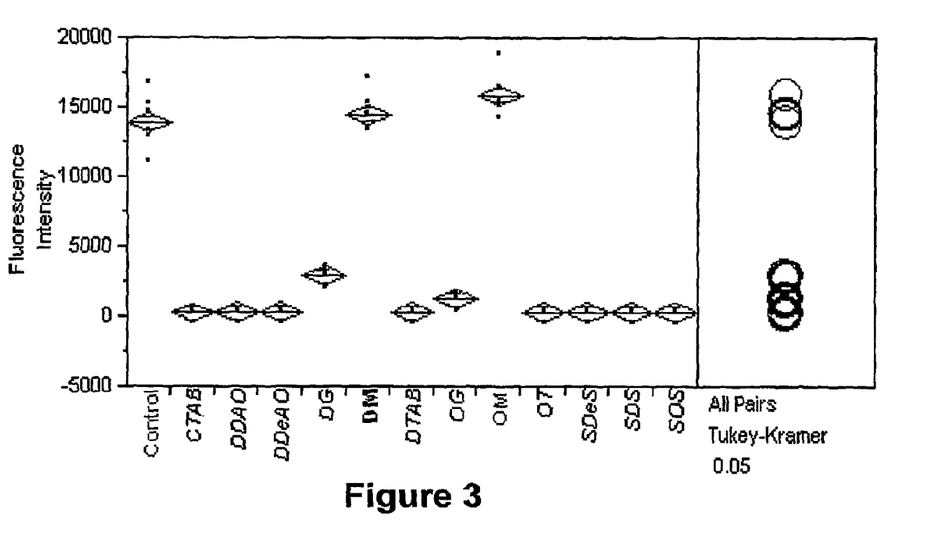
FIG. 3 is a graph showing the potential of various compositions to damage/inhibit cell growth as measured by specific viability dyes and fluorescence intensity measurements. In the comparison of cytotoxicity at 0.1 CMC, red color represents the conditions with no difference with control.

FIGS. 2 and 3 present the screening results of various comparative materials and protective compositions at 0.01 CMC and 0.1 CMC, respectively. The Fluorescence Intensity on the y-axis corresponds to the number of cells present in the vessel which corresponds to cell growth (higher the fluorescence the better) and the x-axis corresponds to the type of composition.

A close analysis of FIGS. 2 and 3 shows that the comparative materials CTAB and DTAB are clearly the most toxic to cells. Microscopic observations confirm that these two surfactants, at the lowest concentration, completely lysed the cells. Also, a commonly assumed strong detergent comparative material, SDS, while inhibitory, was not as effective as a detergent as CTAB and DTAB.

It is also to be noted that, as the concentration approaches the CMC, all but two of the protective compositions, DM and OM, became toxic.

Both the protective compositions DM and OM share the same hydrophilic head group, maltose (FIG. 1), while the protective compositions OG and DG, which have a single glucose head group, but share the same alkyl chain length as the protective compositions OM and DM, respectively, are more toxic.

Figure 4:
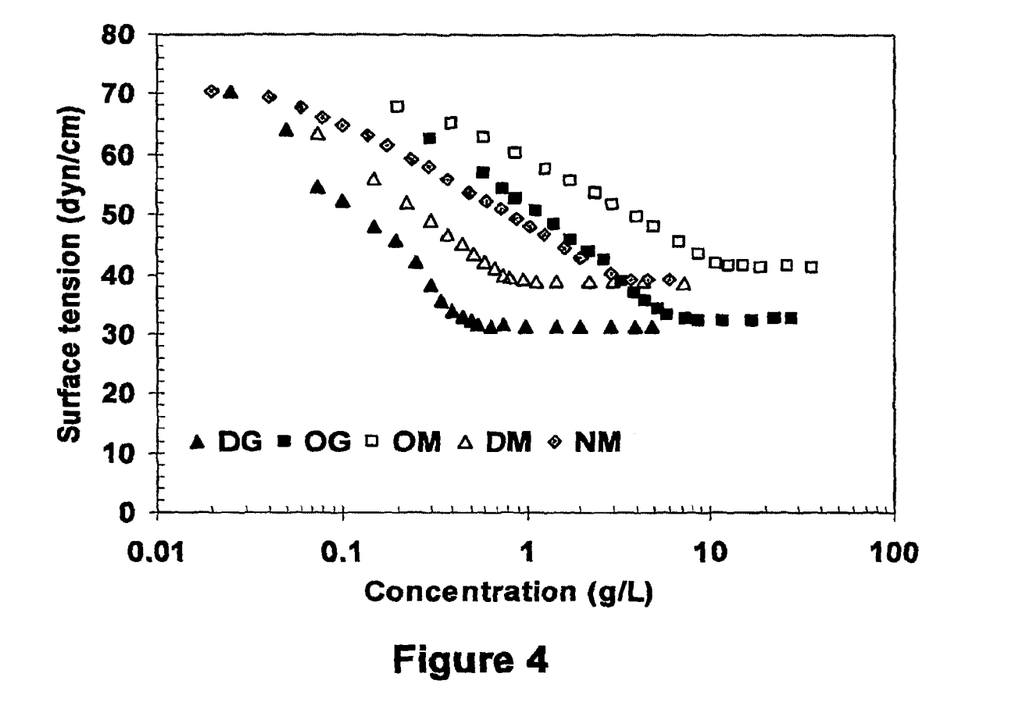
FIG. 4 is a graph showing static surface tension for various compositions. Surface tension of specific materials in cell culture medium at 37° C.: comparative materials: ▲) DG; ■) OG; and protective compositions Δ) DM; □) OM; x) NM.
Figure 5A:
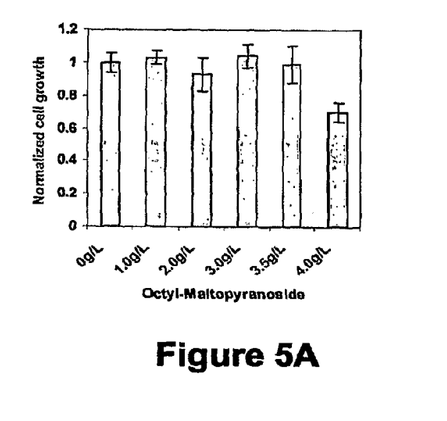
FIGS. 5A, 5B, 5C and 5E are graphs showing cell growth in T-25 flasks for various protective compositions.
Figure 5B:
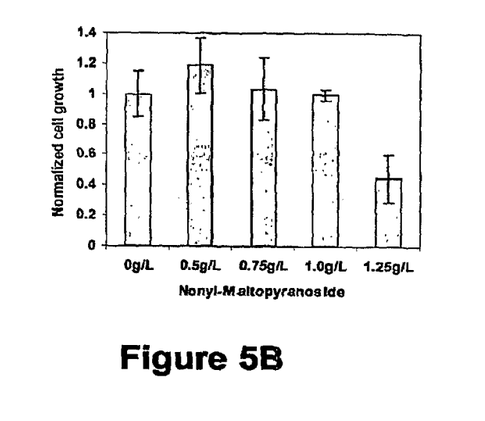
Figure 5C:
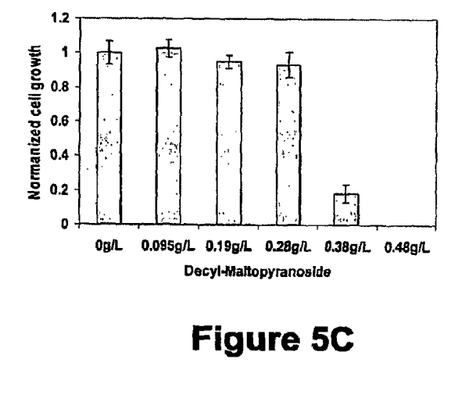
Figure 5D:
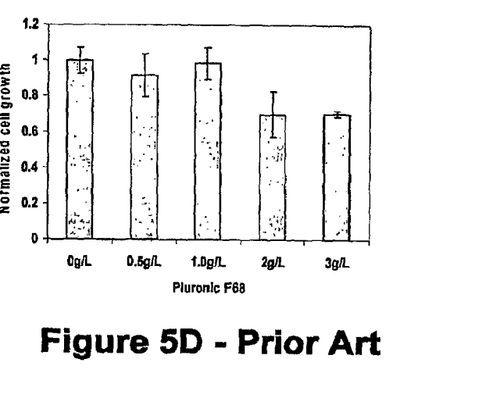
FIG. 5D is a graph showing cell growth in T-25 flasks for a comparative material, Pluronic PF-68® surfactant.
Figure 5E:
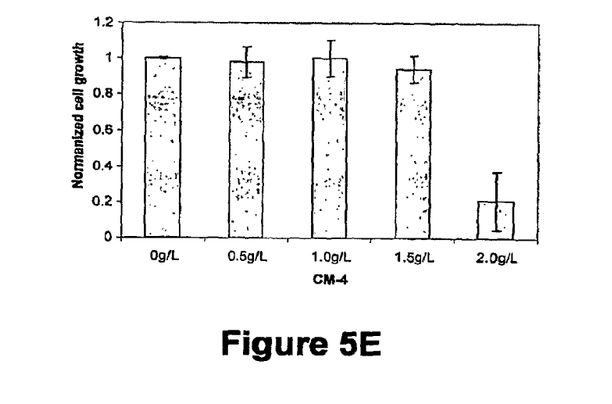

FIG. 4 presents the surface tension of the comparative materials DG, OG, and the protective compositions DM, OM, and NM as a function of concentration in cell culture medium at 37 C. NM was also examined since its structure is between that of OM and DM. Both of the protective compositions with glucose head groups lowered the surface tension the most, and to the same level, while the maltose head group protective compositions lowered the surface tension to the same level (relative to each other), but not as low as the glucose head groups for the comparative materials (OG and DG).

Also, interestingly, for both families of head groups, the protective compositions with the longer chain lengths lowered the surface tension at a lower concentration. While not wishing to be bound by theory, the inventors herein believe that the ultimate lowering of the surface tension is a function of hydrodynamic head group size (Table 2).

TABLE 2

| | HEAD GROUP SIZE (Å$^2$) | CMC SURFACE TENSION (DYN/CM) |
|---|---|---|
| OG | 40 | 32.5 |
| DG | 32 | 31.5 |
| OM | 61 | 41.5 |
| NM | 59 | 40.1 |
| DM | 42 | 38.9 |

Dynamic Surface Tension

One mechanism of protection that the protective compositions provide is to lower the gas-liquid interfacial tension. However, such lowering is not an instantaneous process. A freshly formed bubble has a surface tension very close to that of culture medium without surfactants. The lowering of the surface tension by any molecules requires the diffusion, and subsequent adsorption of the molecules to the gas-liquid interface. Depending on the type and concentration of such molecules, this time frame has been reported to range from milliseconds to days. The resident time of bubbles rising in a bioreactor is normally in the range of seconds. Therefore, another desirable criterion for the protective compositions is to reduce the surface tension rapidly.

Figure 6:
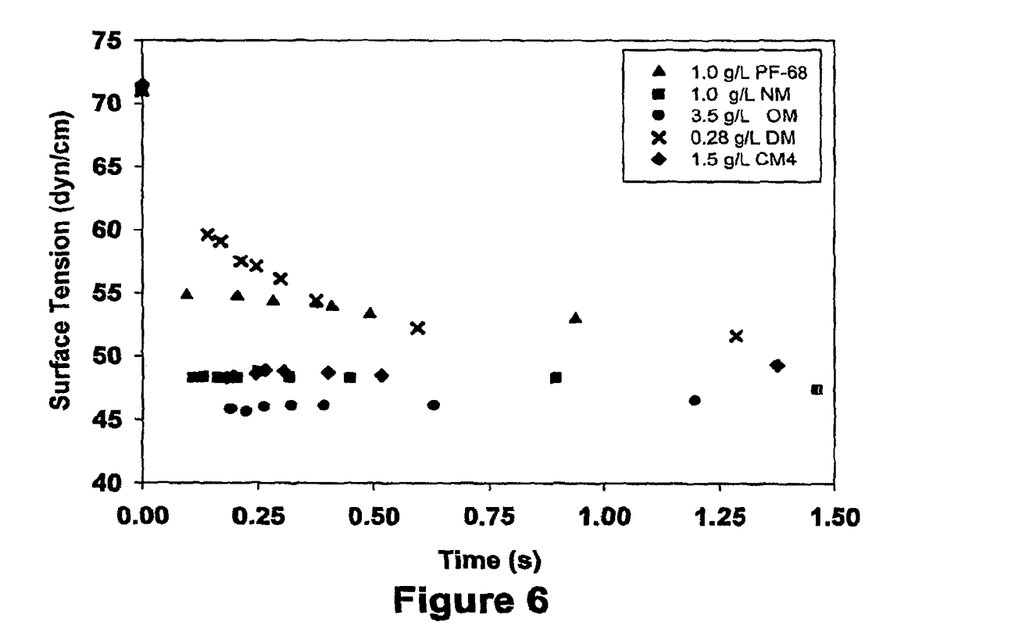
FIG. 6 is a graph showing dynamic surface tension for various compositions in cell culture medium at 37° C.: comparative material ■) 1.0 g/L PF-68® surfactant; and protective compositions Δ) 0.28 g/L DM; □) 3.5 g/L OM; ●) 1.0 g/L NM.

FIG. 6 presents the dynamic surface tension of the four maltopyranosides protective compositions, and the surfactant PF-68® comparative material, at the maximum contraction before inhibitory effects on cell growth was observed (from FIG. 5).

1.0 g/L of the surfactant PF-68® comparative material can rapidly decrease surface tension from 72 dyn/cm to around 55 dyn/cm within 0.1 second, followed by a slow decrease to the equilibrium surface tension reported to be 45 dyn/cm, as determined by the Wilhelmy plate method.

In contrast, the protective compositions OM, NM and CM4 rapidly (less than 0.1 s) lowered the surface tension with very little change after the initial drop, while 0.28 g/L of the protective composition DM took the longest, approximately 0.5 second, to achieve its equilibrium value.

Cell-Bubble Interactions.

Consistent with the techniques used by Ma et al. (2004), the effectiveness of the protective compositions with respect to cell-bubble interactions was evaluated using the bubble collection device. Prior to the studies with cells, the size of the bubbles generated using a sintered glass sparger and a 22 gauge needle and two different concentrations of the PF-68® comparative material and the protective composition NM were determined. The results are presented in Table 3 below.

TABLE 3

Effect of surfactants on bubble size

| | Median Diameter | |
|---|---|---|
| Sparger | Sintered glass (microbubble) | 22 gauge needle (large bubble) |
| 0.03 g/L PF-68 ® | 346 μm | 2.8 mm |
| 1.0 g/L PF-68 ® | 147 μm | 2.7 mm |
| 0.6 g/L NM | 159 μm | 2.7 mm |
| 1.0 g/L NM | 157 μm | 2.5 mm |

As can be observed from an analysis of the data in Table 3, for a given sparger type, only changing the concentration of PF-68 had an effect on bubble size.

Figure 7:
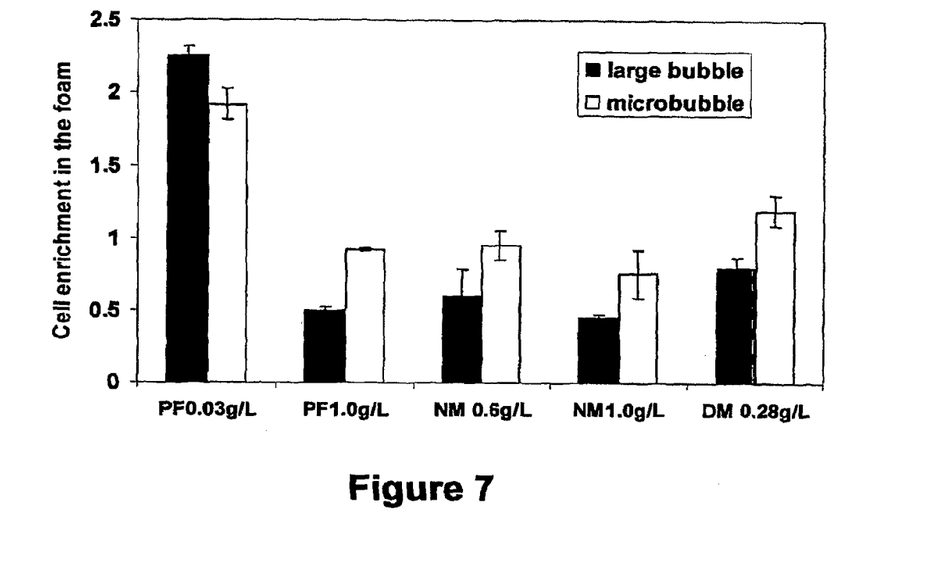
FIG. 7 is a graph showing cell-bubble interactions, as measured by the cell enrichment factor, under different surfactant conditions.

FIG. 7 presents the results of the studies using the bubble collection device and measuring the cell enrichment in the foam as a function of the two different spargers and different types and concentrations of comparative materials and protective compositions. A significant decrease in cell-bubble interactions (measured in this case by a decrease in the enrichment factor) is observed when the concentration of the PF-68® comparative material is increased from 0.03 to 1.0 g/L.

A second observation is that 0.6 g/L of the protective composition NM can achieve the similar effect as 1.0 g/L PF-68® comparative material and increasing NM to 1.0 g/L slightly decreases the enrichments factor further.

The effect of 0.28 g/L of the protective composition DM on the decrease of the enrichment factor was less than PF-68® comparative material and the protective composition NM.

A third observation is that the effect of all of the comparative materials and the protective compositions on the enrichment factor was less for microbubbles than large bubbles.

The potential of a material to create a foam layer was evaluated with the PF-68® comparative material and the protective compositions DM, and NM. Specifically, a parameter, called the foam liquid, which was the ratio of liquid volume collected in the centrifuge tube to the air pumped into the column (measured in standard cubic centimeter, sccm) was measured as a function of different concentrations. The results of this study are presented in FIG. 8.

Figure 8:
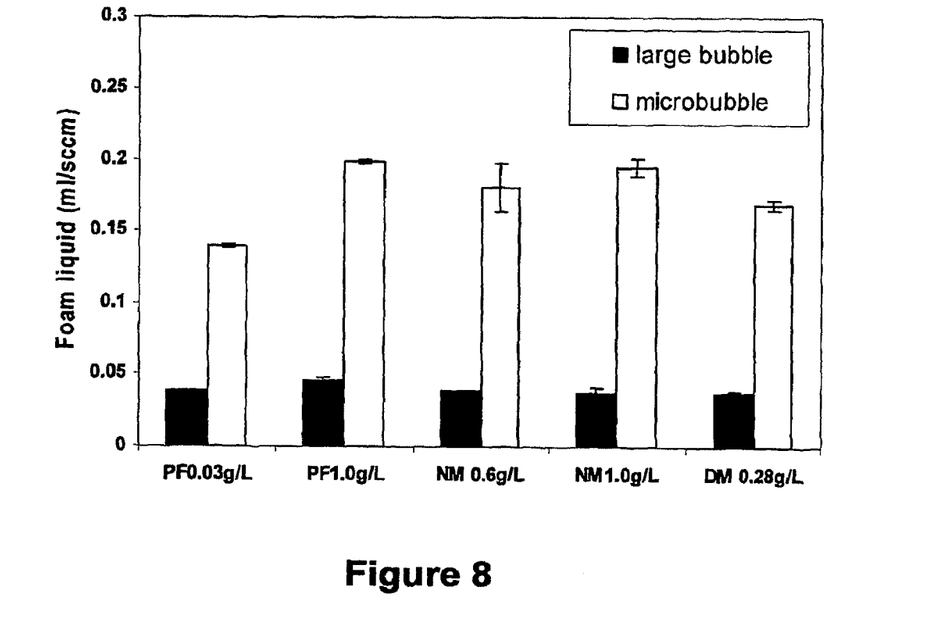
FIG. 8 is a graph showing a comparison of capability of various surfactants and bubble size to form foam, as measured by a factor called the foam liquid.

Interestingly, very little difference in the parameter foam liquid was observed among the comparative materials and the protective compositions, but a uniform, significant difference was observed between large bubbles and microbubbles.

Discussion

In the examples shown herein, three approaches were used to evaluate three attributes needed for a protective composition to be useful to prevent cell-bubble adhesion: i) cytotoxicity testing as measured by potential to inhibit growth, ii) the rapid lowering of the surface tension in cell culture media, and iii) the prevention of cell enrichment in the foam layer.

In a particular aspect, various protective compositions that are considered to be "small molecular weight" compositions were evaluated since: 1) most of the comparative materials are large molecules (i.e. greater than 1000 molecular weight), 2) small molecules have an advantage in downstream purification, such as through the removal by dialysis, 3) in some situations, the PF-68® comparative material can induce the precipitation of concentrated recombinant proteins (van der Pol and Tramper, 1998), 4) the PF-68® comparative material begins to loses its effectiveness as the cell concentration increases, and 5) it is highly advisable to have more than one, FDA approved, protective type of molecule for use in commercial cell cultures.

In the examples shown herein, protective compositions include maltopyranosides and maltosides, a group of nonionic molecules consisting of a maltose moiety linked with cyclic or straight alkyl chains. The maltopyranoside and maltoside protective compositions showed the least cytotoxicity to CHO cells adapted to serum-free medium. The maltopyranoside and maltoside protective compositions are non-crystalline material with high water solubility and are generally used in cosmetic products and as an emulsifier.

The protective compositions were also evaluated in order to quantify the cytotoxicity of the protective compositions with respect to cell growth, not just hemolytic or lytic activity. It is noted that the OM protective composition is less toxic to red blood cells than the OG comparative material.

In addition, the OM and DM protective compositions did not induce hemolysis until 0.2~0.3 CMC. If the cell culture media does not significantly change the CMC of these protective compositions, the point at which the cell growth begins to be inhibited is consistent with this 0.2~0.3 of the CMC rule of thumb. It was also observed that ionic materials were more toxic than nonionic materials. The electrostatic interaction between head groups of the ionic surfactants and zwitterionic hydrophilic moiety of membrane lipid may contribute to their cytotoxicity.

The process of "molecule adsorption to new surface" can be divided into the following steps: 1) diffusion to sub-surface; 2) adsorption from sub-surface to the surface; and 3) reorientation of molecules at the surface.

Diffusion controlled and a mixed kinetic-diffusion models have been proposed reflecting these steps. In the former, the diffusion process is the only rate-controlling step. In the latter, the molecules have to not only diffuse to the surface, but also overcome any potential energy barriers involved in finding an "empty site" and obtain a proper orientation (Eastoe and Dalton, 2000). Given the current understanding of the relatively complex structure of block copolymers at air-water interfaces (i.e., an ordered structure with PO groups in the air and EO groups extending into the water), the smaller molecule sugar protective compositions are now believed by the inventors herein to lower the surface tension more rapidly (i.e., no need for molecule chain rearrangement).

This phenomenon was observed since for the maltoside and all the maltopyranosides but DM. The surface tension, measured in a dynamic mode, rapidly achieved an equilibrium, unlike the PF-68® comparative material which had initial, rapid drop, and then a slow decrease beyond the time of the test. It is also believed by the inventors herein that DM, if issued at the concentration of the other maltopyranosides, will perform, with respect to the dynamic surface tension, in a manner similar to the other maltopyranosides.

The examples herein also verified that the protective compositions added to the cell culture media can significantly and rapidly reduce the surface tension and can reduce cell-bubble attachment. It is interesting to note that, regarding different bubble size, Meier et al. (1999) reported that the cell-bubble attachment played an important role in cell damage when using microbubbles, even with the presence of the PF-68 comparative material.

The inventors herein also observed that the enrichment factor was higher for microbubbles relative to large bubbles. In general, as bubble sizes get smaller, the foam tends to be more stable, thicker, and the relative amount of liquid retained in the fluid between bubbles becomes great for a given amount of gas sparged. Therefore, more cells are retained in the foam created from smaller bubbles relative to larger bubbles. While a surfactant, such as the PF-68® comparative material, reduces and/or prevents cells from actually adhering to gas-liquid interfaces, the surfactant does not prevent the cells from being in the fluid between the bubbles. As such, the inventors herein also believe that the foam structure should be considered when analyzing bubble-associated damage, especially in bioreactors that use aeration strategies that include different bubble sizes.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

The citation of any reference herein is not an admission that such reference is available as prior art to the instant invention. Any publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Therefore, it is intended that the invention not be limited to the particular embodiment disclosed herein contemplated for carrying out this invention, but that the invention will include all embodiments falling within the scope of the claims.

REFERENCES

Arnold, J. J., Ahsan, F., Meezan, E., Pillion, D. J. 2004. Correlation of tetradecyl maltoside induced increases in nasal peptide drug delivery with morphological changes in nasal epithelial cells. *J. Pharm. Sci.* 93: 2205-2213.

Bavarian, F., Fan, S. L., Chalmers, J. J. 1991. Microscopic visualization of insect cell-bubble interactions. I: rising bubbles, air-medium interface, and the foam layer. *Biotechnol. Prog.* 7: 140-150.

Bauer, T., Hancock, L., Rathman, J., Chalmers, J. J., 2000. Cell-Microcarrier adhesion to Gas-Liquid Interfaces and Foam, Biotechnol Prog 16:125-132.

Chalmers, J. J., Bavarian, F. 1991. Microscopic visualization of insect cell-bubble interactions, II: the bubble film and bubble rupture. *Biotechnol. Prog.* 7: 151-158.

Chattopadhyay, D., Rathman, J. F., Chalmers, J. J. 1995a. The protective effect of specific medium additives with respect to bubble rupture. *Biotechnol. Bioeng.* 45: 473-80.

Chattopadhyay, D., Rathman, J., Chalmers, J. J. 1995b. A thermodynamic explanation for cell adhesion to gas-liquid interfaces. *Biotechnol. Bioeng.* 48: 649-658.

Chisti, Y. 2000. Animal-cell damage n sparged bioreactors. *Trends Biotechnol.* 18: 420-432.

Claesson, P. M., Kjellin, U. R. M. 2002. Sugar surfactants. In: Encyclopedia of surface and colloid science. (Hubbard, A. T. ed.) Marcel Dekker, New York.

de la Maza, A., Coderch, L., Gonzalez, P., Parra, J. L. 1998. Subsolubilizing alterations caused by alkyl glucoside in phosphatidylcholine liposomes. *J. Control. Release* 52: 159-168.

Dey, D., Emery, A. N. 1999. Problems in predicting cell damage from bubble bursting. *Biotechnol. Bioeng.* 65: 240-245.

deZengotita, V. M., Schmelzer, A. E., Miller, W. M. 2002. Characterization of hybridoma cell responses to elevated pCO2 and osmolality: intracellular pH, cell size, apoptosis, and metabolism. *Biotechnol. Bioeng.* 77: 369-380.

Dickson, A. J. 1998. Apoptosis regulation and its application to biotechnology. *Trends Biotechnol.* 16: 339-342.

Eastoe, J., Dalton, J. S. 2000. Dynamic surface tension and adsorption mechanisms of surfactants at the air-water interface. *Adv. Colloid Interface Sci.* 85:103-144.

Ericsson, C. A., Soederman, O., Garamus, V. M., Bergstroem, M., Ulvenlund, S. 2005. Effects of temperature, salt, and deuterium oxide on the self-aggregation of alkyl-glycosides in dilute solution. 2. n-tetradecyl-β-D-maltoside. *Langmuir,* 21:1507-1515.

Fazilet, V. S. 1998. Foaming: consequences, prevention and destruction. *Biotechnology Advances,* 16:913-948.

Garcia-Briones, M. A., Brodkey, R. S., Chalmers, J. J. 1994. Computer simulations of the rupture of a gas bubble at a gas-liquid interface and its implications in animal cell damage. *Chem. Eng. Sci.* 49: 2301-2320.

Goldblum, S., Bea, Y. K., Hink, W. F., Chalmers, J. J. 1990. Protective effect of methylcellulose and other polymers on insect cells subjected to laminar shear stress. *Biotechnol. Prog.* 6: 383-390.

Handa-Corrigan, A., Weeratunge, N. P., Braybrook, J. H., Mackay, G. A., Chescoe, D. 1997. Animal cell technology, from vaccines to genetic medicine (Carrondo, M. J. T., Griffiths, B., Moreira, J. L. P. eds, pp. 121-126. Butterworth-Heinemann.

Jordan, M., Sucker, H., Einsele, A., Widmer, F., Eppenberger, H. M. 1994. Interactions between animal cells and gas bubbles: the influence of serum and Pluronic F68 on the physical properties of the bubble surface. *Biotechnol. Bioeng* 43: 446-454.

Kilburn, D. G., Webb, F. C. 1968. The cultivation of animal cells at controlled dissolved oxygen partial pressure. *Biotechnol. Bioeng.* 10: 801-814.

Kunas, K. T., Papoutsakis, E. T. 1989. Increasing serum concentrations decrease cell death and allow growth of hybridoma cells at higher agitation rates. *Biotechnol. Lett.* 11: 525-530.

Langheinrich, C., Nienow, A. W., Eddleston, T., Stevenson, N. C., Emery, A. N., Clayton, T. M., Slater, N K H. 2002. Oxygen transfer in stirred bioreactors under animal cell culture conditions. *Food Bioproduct Proc (Trans I Chem E, Part C).* 80: 38-44.

Ma. N., Chalmers, J. J., Aunins, J. G., Zhou, W. Xie, L. 2004. Quantitative Studies of Cell-Bubble Interactions and Cell Damage at Different Pluronic F-68 and Cell Concentrations. *Biotechnol. Prog.* 20: 1183-1191.

Ma, Y., Hsu, C. 1997. Protein denaturation by combined effect of shear and air-liquid interface. *Biotechnol. Bioeng.* 54:503-512.

Marie, M. L., Champeil, P., Moller, J. V., 2000. Interaction of membrane proteins and lipids with solubilizing detergents. *Biochimica et Biophysica Acta.* 1508: 86-111.

Meier, S. J., Hatton, T. A., Wang, D. I. C. 1999. Cell death from bursting bubbles: role of cell attachment to rising bubbles in sparged reactors. *Biotechnol. Bioeng.* 62: 468-478.

Michaels, J. D., Nowak, J. E., Mallik, A. K., Koczo, K., Wasan, D. T., Papoutskis, E. T. 1995. Analysis of cell-to-bubble attachment in sparged bioreactors in the present of cell-protecting additives. *Biotechnol. Bioeng.* 47: 407-419.

Michaels, J. D., Kunas, K. T., Papoutsakis, E. T. 1992. Fluid-mechanical damage of freely-suspended animal cells in agitated bioreactors: effects of dextran, derivatized celluloses and polyvinyl alcohol. *Chem. Eng. Commun.* 118: 341-360.

Michaels, J. D., Papoutsakis E. T. 1991. Polyvinyl alcohol and polyethylene glycol as protectants against fluid-mechanical injury of freely-suspended animal cells (CRL 8018). *J. Biotechnol.* 19: 241-258.

Mostafa, S. S., Gu. X. 2003. Strategies for improved dCO2 removal in large-scale fed-batch cultures. *Biotechnol. Prog.* 19: 45-51.

Murhammer, D. W., Goochee, C. F. 1990. Structural features of nonionic polyglycol polymer molecules responsible for the protective effect in sparged animal cell bioreactors. *Biotechnol. Prog.* 6: 142-148.

Neimert-Andersson, Sauer, S., Panknin, O., Borg, T., Soderlined, E., Somfai, P. 2006. Synthesis of New Sugar-Based Surfactants and Evaluation of Their Hemolytic Activities. J. Org. Chem. 71:3623-3626.

Nienow, A. W. 2006. Reactor engineering in large scale animal cell culture. *Cytotechnology.* 50: 9-33.

Niagam, P. 2006. Interaction of water-soluble surfactants with self-assembled lipid monolayers at the vapor-liquid interface: equilibrium and dynamic phenomena. PhD thesis. The Ohio State University.

Osman, J. J., Birch, J., Varley, J. 2001. The response of GS-NSO myeloma cells to pH shifts and pH perturbations. *Biotechnol. Bioeng.* 75: 63-73.

Ozturk, S. S. 2006. Cell culture technology—an overview. *Biotechnology and Bioprocessing.* 30:1-13.

Ozturk, S. S. 1996. Engineering challenges in high-density cell culture systems. *Cytotechnology,* 22: 3-16.

Pashley, T. M., Karaman, M. E. 2004. Applied colloid and surface chemistry. John Wiley & Sons Ltd, West Sussex, England.

Qi, H. N. 2001. Membrane and micro-sparging aerations in long-term high-density perfusion cultures of animal cells. PhD thesis. Oregon State University.

Pugh, R. J. 1996. Foaming, foam films, antifoaming and defoaming. *Adv. Colloid interface Sci.* 64: 67-142.

Runyan, W. S., Geyer, R. P. 1963. Growth of L cell suspensions on a Warberg apparatus. *Proc. Soc. Biol. Med.* 112: 1027-1030.

Ryll, T., Valley, U., Wagner, R. 1994. Biochemistry of growth inhibition by ammonium ions in mammalian cells. *Biotechnol. Bioeng.* 44: 184-193.

Söderlind, E., Karlsson, L. 2006. Haemolytic activity of maltopyranoside surfactants. *Eur. Pharm. Biopharm,* 62: 254-259.

Söderlind, E., Wollbratt, M., von Gorswant, C. 2003. The usefulness of sugar surfactants as solubilizing agents in parenteral formulations. *Int. J. Pharm.* 252: 61-71.

Swim, H. E., Parker, R. F. 1960. Effect of Pluronic F68 on growth of fibroblasts in suspension on rotary shaker. *Proc. Soc. Exp. Biol. Med.* 103: 252-254.

Taylor, D. J. F., Thomas, R. K., Penfold, J. 2007. Polymer/surfactant interactions at the air/water interface. Advances in Colloid and Interface Science 132:69-110.

Trinh, K., Garcia-Briones, M., Hink, F., Chalmers, J. J. 1994. Quantification of damage to suspended insect cells as a result of bubble rupture. *Biotechnol. Bioeng.* 43:37-45.

van der Pol, L. A., Paijens, I., Tramper, J. 1995. Dextran as protectant against damage caused by sparging for hybridoma cells in a bubble column. *J. Biotechnol.* 43: 103-110.

van der Pol, L., Tramper, J. 1998. Shear sensitivity of animal cells from a culture-medium perspective. *TIBTECH,* 16: 323-328.

Wu, J. 1995. Mechanisms of animal cell damage associated with gas bubbles and cell protection by medium additives. *J. Biotechnol.* 43: 81-94.

Wu, J., Daugulis, A. J., Faulkner, P., Goosen, M. F. A. 1995, Protective effects of polymer additives on animal cells exposed to rapidly falling liquid film. *Biotechnol. Prog.* 11: 127-132.

Yang, A., Cardona, D. L., Barile, F. A. 2002. In vitro cytotoxicity testing with fluorescence-based assays in cultured human lung and dermal cells. *Cell Biology Toxicology,* 18:97-108.

Zhou, W., Rehm, J., Hu, W. 1995. High viable cell concentration fed-batch cultures of hybridoma cells through online nutrient feeding. *Biotechnol. Bioeng.* 46: 579-587.

Zhu, M. M., Goyal, A., Rank, D. L., Gupta, S. K., Vanden Boom, T., Lee, S. S. 2005. Effect of elevated pCO2 and osmolality on growth of CHO cells and production of antibody-fusion protein B1: a case study. *Biotechnol. Prog.* 21: 70-77.

What is claimed is:

1. A method for reducing gas-cell surface interface damage, comprising culturing cells in the presence of an effective amount of one or more protective compositions, the protective composition comprising a maltopyranoside or a maltoside compound having a C1-C15 alkyl moiety, and a sugar moiety having at least two closed rings therein, the sugar moiety providing a hydrophilic component to the protective composition, and the alkyl moiety providing a hydrophobic component to the protective composition.

2. The method of claim 1, wherein the sugar moiety comprises an alkyl-β-D-maltoside.

3. The method of claim 1, wherein the alkyl moiety ranges from C6 to C10.

4. The method of claim 1, wherein the alkyl moiety is a saturated or unsaturated, substituted or unsubstituted, straight, branched or ring hydrocarbon.

5. The method of claim 1, wherein the protective composition is present in an amount ranging from about 0.1 g/L to about 4.0 g/L.

6. The method of claim 1, wherein at least the sugar moiety comprises at least one of: n-Octyl-β-D-maltopyranoside (OM), n-Nonyl-β-D-maltopyranoside (NM), n-Decyl-β-D-maltopyranoside (DM), and cyclohexyl-butyl-maltopyranoside (CM-4).

7. The method of claim 5, wherein the protective composition comprises one or more of: about 3.5 g/L or less octyl maltopyranoside; about 1.0 g/L or less nonyl maltopyranoside; about 0.28 g/L or less decyl maltopyranoside; and about 1.5 g/L or less cyclohexyl-butyl-maltopyranoside (CM-4).

8. A method of modifying a cellular surface so as to confer resistance to adherence of gas bubbles, or gas-medium interfaces, in a medium containing one or more cells, the method comprising adding to the medium an effective amount of at least one protective composition under conditions in which the protective composition confers resistance to adherence of gas bubbles to the cell and/or the cells to gas-liquid interfaces, the protective composition comprising a maltopyranoside or a maltoside compound having a C4-C10 alkyl moiety, and a sugar moiety having at least two closed rings therein, the sugar moiety providing a hydrophilic component to the protective composition, and the alkyl moiety providing a hydrophobic component to the protective composition.

9. A method for recovering one or more desired products from host cells comprising:
providing a source of cells having or producing at least one desired product;
providing a protective composition, the protective composition comprising a maltopyranoside or a maltoside compound having a C4-C10 alkyl moiety, and a sugar moiety having at least two closed rings therein, the sugar moiety providing a hydrophilic component to the protective composition, and the alkyl moiety providing a hydrophobic component to the protective composition; and
contacting the cells with the protective composition in an amount effective to reduce adhesion of one or more gas bubbles to the cells.

10. The method according to claim 1, wherein the cells comprise prokaryotic or eukaryotic cells.

11. The method according to claim 1, wherein the cells comprise bacterial, yeast, insect, animal, algae or plant cells.

12. The method according to claim 8, wherein the protective composition is present in an amount ranging from about 0.1 g/L to about 4.0 g/L.

13. A kit for culturing biological cell cultures comprising one or more protective compositions, the protective composition comprising a maltopyranoside or a maltoside compound having a C4-C10 alkyl moiety, and a sugar moiety having at least two closed rings therein, the sugar moiety providing a hydrophilic component to the protective composition, and the alkyl moiety providing a hydrophobic component to the protective composition.

14. The method according to claim 8, wherein the cells comprise prokaryotic or eukaryotic cells.

15. The method according to claim 8, wherein the cells comprise bacterial, yeast, insect, animal, algae or plant cells.

16. The method according to claim 9, wherein the protective composition is present in an amount ranging from about 0.1 g/L to about 4.0 g/L.

17. The method according to claim 9, wherein the cells comprise prokaryotic or eukaryotic cells.

18. The method according to claim 9, wherein the cells comprise bacterial, yeast, insect, animal, algae or plant cells.

* * * * *

UNITED STATES PATENT AND TRADEMARK OFFICE
CERTIFICATE OF CORRECTION

PATENT NO. : 8,440,800 B2  
APPLICATION NO. : 12/438681  
DATED : May 14, 2013  
INVENTOR(S) : Jeffrey J. Chalmers et al.

Page 1 of 1

It is certified that error appears in the above-identified patent and that said Letters Patent is hereby corrected as shown below:

In the Claims:

Column 18, Line 4, Claim 6, after wherein, please delete "at least".

Signed and Sealed this  
Twenty-fifth Day of June, 2013

Teresa Stanek Rea  
*Acting Director of the United States Patent and Trademark Office*